US008747868B2

(12) United States Patent
Bui et al.

(10) Patent No.: US 8,747,868 B2
(45) Date of Patent: Jun. 10, 2014

(54) REACTION PRODUCT OF A POLAR MODIFIED POLYMER AND AN ALKOXYSILANE AND A COMPOSITION CONTAINING THE REACTION PRODUCT

(75) Inventors: Hy Si Bui, Piscataway, NJ (US); Anita Tong, Westfield, NJ (US); Maria Pia Rossi, New Brunswick, NJ (US)

(73) Assignee: L'Oreal, Paris (FR)

( * ) Notice: Subject to any disclaimer, the term of this patent is extended or adjusted under 35 U.S.C. 154(b) by 568 days.

(21) Appl. No.: 12/982,108

(22) Filed: Dec. 30, 2010

(65) Prior Publication Data
US 2012/0171140 A1 Jul. 5, 2012

(51) Int. Cl.
*A61K 9/00* (2006.01)

(52) U.S. Cl.
USPC ........................................................ 424/400

(58) Field of Classification Search
None
See application file for complete search history.

(56) References Cited

U.S. PATENT DOCUMENTS

| | | | |
|---|---|---|---|
| 2,957,838 A | 10/1960 | Mills, Jr. | |
| 3,590,076 A | 6/1971 | Heintzelman et al. | |
| 3,699,154 A | 10/1972 | Heintzelman et al. | |
| 3,933,511 A | 1/1976 | Heintzelman et al. | |
| 3,933,512 A | 1/1976 | Heintzelman et al. | |
| 4,041,056 A | 8/1977 | Heintzelman et al. | |
| 4,226,889 A | 10/1980 | Yuhas | |
| 4,420,588 A | 12/1983 | Yoshioka et al. | |
| 4,693,935 A | 9/1987 | Mazurek | |
| 4,725,658 A | 2/1988 | Thayer et al. | |
| 4,824,906 A * | 4/1989 | Honsberg et al. | 525/74 |
| 4,871,536 A | 10/1989 | Arraudeau et al. | |
| 4,972,037 A | 11/1990 | Garbe et al. | |
| 4,981,902 A | 1/1991 | Mitra et al. | |
| 4,981,903 A | 1/1991 | Garbe et al. | |
| 5,032,391 A | 7/1991 | Helioff et al. | |
| 5,209,924 A | 5/1993 | Garbe et al. | |
| 5,334,737 A | 8/1994 | Thimineur et al. | |
| 5,389,363 A | 2/1995 | Snyder et al. | |
| 5,466,477 A | 11/1995 | Sevenich | |
| 5,618,524 A | 4/1997 | Bolich et al. | |
| 5,620,693 A | 4/1997 | Piot et al. | |
| 5,800,816 A | 9/1998 | Brieva et al. | |
| 5,891,914 A | 4/1999 | Haney | |
| 5,911,974 A | 6/1999 | Brieva et al. | |
| 5,965,112 A | 10/1999 | Brieva et al. | |
| 5,985,298 A | 11/1999 | Brieva et al. | |
| 5,998,547 A | 12/1999 | Hohner | |
| 6,045,782 A | 4/2000 | Krog et al. | |
| 6,126,929 A | 10/2000 | Mougin | |
| 6,274,152 B1 | 8/2001 | Brieva et al. | |
| 6,338,839 B1 | 1/2002 | Auguste et al. | |
| 6,464,964 B1 | 10/2002 | Brieva et al. | |
| 6,482,400 B1 | 11/2002 | Collin | |
| 6,492,455 B1 | 12/2002 | Nadolsky | |
| 6,524,564 B1 | 2/2003 | Kim et al. | |
| 6,562,322 B2 | 5/2003 | Brieva et al. | |
| 6,716,419 B2 | 4/2004 | Zoltowski et al. | |
| 6,780,422 B2 | 8/2004 | Brieva et al. | |
| 6,958,148 B1 | 10/2005 | Green et al. | |
| 6,964,773 B1 | 11/2005 | Morrison | |
| 7,005,134 B2 | 2/2006 | Brieva et al. | |
| 7,160,550 B2 | 1/2007 | Brieva et al. | |
| 7,186,766 B2 | 3/2007 | Harashina et al. | |
| 7,314,904 B2 | 1/2008 | Nadolsky et al. | |
| 7,423,104 B2 | 9/2008 | Lion | |
| 7,682,621 B2 | 3/2010 | Lamberty et al. | |
| 7,842,285 B2 | 11/2010 | Lu et al. | |
| 7,875,265 B2 | 1/2011 | Blin et al. | |
| 7,879,316 B2 | 2/2011 | Ferrari et al. | |
| 8,119,110 B2 | 2/2012 | Blin et al. | |
| 2003/0026816 A1 | 2/2003 | Zoltowski et al. | |
| 2003/0082218 A1 | 5/2003 | Ichinohe et al. | |
| 2003/0147931 A1 | 8/2003 | Brieva et al. | |
| 2003/0182734 A1 | 10/2003 | Desenne et al. | |
| 2004/0170586 A1 | 9/2004 | Ferrari et al. | |
| 2004/0186308 A1 | 9/2004 | Koch et al. | |
| 2004/0223986 A9 | 11/2004 | Boussouira et al. | |
| 2005/0013992 A1 | 1/2005 | Azad et al. | |
| 2005/0180936 A1 | 8/2005 | Pays | |
| 2005/0220728 A1 | 10/2005 | Kanji et al. | |
| 2006/0013840 A1 | 1/2006 | Lamberty et al. | |
| 2006/0084764 A1 | 4/2006 | Hanna et al. | |
| 2006/0093568 A1 | 5/2006 | Blin et al. | |
| 2006/0104940 A1 | 5/2006 | Heinrichs et al. | |
| 2006/0110345 A1 | 5/2006 | Lu et al. | |
| 2006/0115444 A1 | 6/2006 | Blin et al. | |
| 2006/0147396 A1 | 7/2006 | Monello | |

(Continued)

FOREIGN PATENT DOCUMENTS

BR 0602495 A 2/2008
DE 100 64 799 A1 6/2002

(Continued)

OTHER PUBLICATIONS

International Cosmetic Ingredient Dictionary and Handbook (9th ed. 2002), published by the CTFA, 1101 17th Street, N.W., Suite 300, Washington, DC 20036-4702.
U.S. Appl. No. 12/981,867, filed Dec. 30, 2010, Bui et al.
U.S. Appl. No. 12/982,108, filed Dec. 30, 2010, Bui et al.
U.S. Appl. No. 12/982,061, filed Dec. 30, 2010, Bradshaw et al.
U.S. Appl. No. 12/981,839, filed Dec. 30, 2010, Bradshaw et al.
U.S. Appl. No. 12/981,882, filed Dec. 30, 2010, Bradshaw et al.
European Office Action Issued Feb. 22, 2013 in Patent Application No. 10 167 788.8.
Hauthal, H. G. Basics, Ingredients, Detergents, Product Safety and Sustainability. Tenside Surf. Det. Jan. 2008, 45 (1), 30-42.

(Continued)

*Primary Examiner* — Paul Dickinson
(74) *Attorney, Agent, or Firm* — Oblon, Spivak, McClelland, Maier & Neustadt, L.L.P.

(57) ABSTRACT

The invention relates to a reaction product of a polar modified polymer and an alkoxysilane having at least one solubilizing functional group and at least one amino substituent.

20 Claims, No Drawings

(56) References Cited

U.S. PATENT DOCUMENTS

| | | |
|---|---|---|
| 2006/0147402 A1 | 7/2006 | Blin et al. |
| 2006/0159642 A1 | 7/2006 | Hanna et al. |
| 2006/0165626 A1 | 7/2006 | Ricard et al. |
| 2006/0188459 A1 | 8/2006 | Heinrichs et al. |
| 2007/0031361 A1 | 2/2007 | Herrmann et al. |
| 2007/0092468 A1 | 4/2007 | Brieva et al. |
| 2007/0093619 A1 | 4/2007 | Bui et al. |
| 2007/0110700 A1 | 5/2007 | Wells et al. |
| 2007/0110702 A1 | 5/2007 | Ehara |
| 2007/0134181 A1 | 6/2007 | Shimizu et al. |
| 2007/0212315 A1 | 9/2007 | Pastor et al. |
| 2007/0256700 A1 | 11/2007 | Bodelin |
| 2007/0258932 A1 | 11/2007 | Bui et al. |
| 2007/0259012 A1 | 11/2007 | Castro et al. |
| 2008/0025934 A1 | 1/2008 | Lebre et al. |
| 2008/0166309 A1 | 7/2008 | McDermott et al. |
| 2008/0171006 A1 | 7/2008 | Bui et al. |
| 2008/0207871 A1 | 8/2008 | Seiler et al. |
| 2008/0305061 A1 | 12/2008 | Bui et al. |
| 2009/0060959 A1 | 3/2009 | Igarashi |
| 2009/0130037 A1 | 5/2009 | Thevenet et al. |
| 2009/0252804 A1* | 10/2009 | Koecher et al. ............ 424/489 |
| 2010/0310489 A1 | 12/2010 | Barba |
| 2010/0330012 A1 | 12/2010 | Bui et al. |
| 2010/0330015 A1 | 12/2010 | Bui et al. |
| 2010/0330016 A1 | 12/2010 | Bui et al. |
| 2010/0330017 A1 | 12/2010 | Bui et al. |
| 2010/0330022 A1 | 12/2010 | Bui et al. |
| 2010/0330024 A1 | 12/2010 | Bui et al. |
| 2011/0020254 A1 | 1/2011 | Bui et al. |
| 2011/0020255 A1 | 1/2011 | Bui et al. |
| 2011/0020256 A1 | 1/2011 | Bui et al. |
| 2011/0020257 A1 | 1/2011 | Bui et al. |
| 2011/0020260 A1 | 1/2011 | Bui et al. |
| 2011/0020261 A1 | 1/2011 | Bui et al. |
| 2011/0020263 A1 | 1/2011 | Ilekti et al. |
| 2011/0021681 A1 | 1/2011 | Bui et al. |
| 2011/0021683 A1 | 1/2011 | Bui et al. |
| 2011/0038819 A1 | 2/2011 | Bui et al. |
| 2011/0223122 A1 | 9/2011 | Bui et al. |
| 2011/0223123 A1 | 9/2011 | Bui et al. |
| 2011/0280817 A1 | 11/2011 | Ramadan et al. |
| 2011/0280818 A1 | 11/2011 | Kawaratani et al. |
| 2011/0280820 A1 | 11/2011 | Bui et al. |
| 2011/0286950 A1 | 11/2011 | Bui et al. |
| 2011/0286951 A1 | 11/2011 | Bui et al. |
| 2011/0293550 A1 | 12/2011 | Bui et al. |
| 2011/0311467 A1 | 12/2011 | Bui et al. |
| 2012/0004327 A1 | 1/2012 | Bui et al. |
| 2012/0107263 A1 | 5/2012 | Bui et al. |
| 2012/0171137 A1 | 7/2012 | Bradsaw et al. |
| 2012/0171139 A1 | 7/2012 | Bradshaw et al. |

FOREIGN PATENT DOCUMENTS

| | | |
|---|---|---|
| DE | 102004008941 A1 | 9/2005 |
| EP | 571 882 | 5/1993 |
| EP | 0 890 583 A1 | 7/1998 |
| EP | 1 314 415 A1 | 5/2003 |
| EP | 1 854 451 A2 | 11/2007 |
| EP | 2 036 536 A1 | 3/2009 |
| EP | 2269568 A2 | 1/2011 |
| EP | 2343040 A2 | 7/2011 |
| FR | 2 789 896 | 8/2000 |
| FR | 2926984 A1 | 8/2009 |
| JP | A-07053921 | 2/1995 |
| JP | 2009-143825 | 7/2009 |
| WO | WO 96/03967 A1 | 2/1996 |
| WO | WO 01/17485 | 3/2001 |
| WO | WO 01/22932 | 4/2001 |
| WO | WO 01/32737 | 5/2001 |
| WO | WO 02/088456 A1 | 11/2002 |
| WO | WO 02 098379 A1 | 12/2002 |
| WO | WO 03/042221 | 5/2003 |
| WO | WO 2006/112690 A1 | 10/2006 |
| WO | WO 2006/127883 A2 | 11/2006 |
| WO | WO 2007/048672 A1 | 5/2007 |
| WO | WO 2007/096400 A1 | 8/2007 |
| WO | WO 2007/139812 A2 | 12/2007 |
| WO | WO 2008/046763 A1 | 4/2008 |
| WO | WO 2009/085888 A1 | 7/2009 |

OTHER PUBLICATIONS

Vertellus, ZeMac(R) E400 Copolymer Technical Data Sheet, May 29, 2008.
European Search Report dated Mar. 10, 2011, in European Application No. 10167784.7.
European Office Action from European Patent Application No. 10167784.7 dated Mar. 21, 2011 (4 pages).
L. Rudnick, Synthesis, Mineral Oils, and Bio-Based Lubricants, Chemistry and Technology, 2011.
Perstorp, Bottom® H20 product data sheet dated Jan. 3, 2008.
Perstorp, Determination of Viscosity for Boltorn Dendritic Polymers, Aug. 23, 2011.
Mulkern et al. Polymer, 2000, 41 (9), 3193-3203.
Bergbreiter et al. Tetrahedron Letters, 1997, 38 (21), 3703-3706.
European Search Report issued Apr. 8, 2011, in European Patent Application No. 10167791.2 (with English Abstract).
European Search Report issued Mar. 21, 2011, in European Application No. 10167792.0.
European Search Report issued Apr. 6, 2011, in European Patent Application No. 10167794.6.
European Search Report dated Mar. 14, 2011, issued in European Application No. 10167785.4.
European Patent Office Communication dated Apr. 18, 2011, issued in European Application No. 10167785.4.
European Search Report issued Mar. 10, 2011, in European Application No. 10167790.4.
European Office Action issued in European Patent Application No. 10167790.4 dated Mar. 21, 2011 (4 pages).
International Search Report issued May 20, 2010 in PCT/US09/067332 filed Dec. 9, 2009.
International Search Report issued Aug. 11, 2010 in PCT/US09/68246 filed Dec. 16, 2009.
International Search Report Issued Jul. 26, 2010 in PCT/US09/068151 filed Dec. 16, 2009.
International Search Report issued Jul. 28, 2010 in PCT/US09/68251 filed Dec. 16, 2009.
International Search Report issued Jul. 30, 2010 in PCT/US09/68148 filed Dec. 16, 2009.
http://www.Chemical Book.com/ChemicalProductProperty_EN_CB3748204.htm, Poly (methyl vinyl ether-alt-maleic anhydride), 2010.
International Search Report Issued Jul. 30, 2010 in PCT/US09/068146 filed Dec. 16, 2009.
International Search Report issued Jul. 23, 2010 in PCT/US09/68245 filed Dec. 16, 2009.
Extended European Search Report Issued Nov. 29, 2012 in Patent Application No. 08867867.7.
International Search Report issued May 31, 2010 in PCT/US09/067338 filed Dec. 9, 2009.
International Preliminary Report on Patentability issued Jul. 11, 2013, in PCT/EP2011/074209.
Dow Corning 670 Fluid, http:/www.dowcorning.com/applications/search/products/details.aspx?prod=0402387&type=PROD, Jun. 19, 2013.

* cited by examiner

REACTION PRODUCT OF A POLAR MODIFIED POLYMER AND AN ALKOXYSILANE AND A COMPOSITION CONTAINING THE REACTION PRODUCT

FIELD OF THE INVENTION

The present invention relates to a reaction product of a polar modified polymer and an alkoxysilane having at least one solubilizing functional group and at least one amino substituent, as well as a composition comprising the reaction product. The reaction product and composition containing said reaction product have industrial, pharmacological and/or cosmetic applicability and can act as a carrier or matrix for desired agents.

BACKGROUND OF THE INVENTION

It is desirable to formulate products and to make them available to consumers in various forms such as in anhydrous, aqueous and emulsion types of compositions. It is also desirable that these products have long wearing and transfer-resistant properties, that is, they adhere longer to surfaces and substrates such as keratinous materials. One way of achieving these properties is through the use of film forming resins such as silicone film forming resins in anhydrous systems. However, one drawback associated with their use is that they tend to be brittle and flake off.

Another way of achieving long wearing and transfer-resistant properties is to employ latex film-formers in oil-in-water emulsions which help improve the adhesion of the compositions to surfaces and keratinous materials. However, latex film formers can be difficult to formulate with due to the large solid content load required, making them unstable, or sensitive to added ingredients. Moreover, the formulation of emulsions which use traditional surfactants or emulsifying agents can pose challenges with respect to stability and effective delivery of beneficial ingredients or desired agents.

Thus, there remains a need for improved products which have long-wearing and transfer-resistant properties, which can be made available in various types of compositions such as anhydrous, aqueous and emulsion types, and which can also function as a carrier and/or matrix for desired agents.

BRIEF SUMMARY OF THE INVENTION

The present invention relates to a reaction product of at least one polar modified polymer and at least one alkoxysilane having at least one solubilizing functional group and at least one amino substituent.

The present invention also relates to compositions containing a reaction product of at least one polar modified polymer and at least one alkoxysilane having at least one solubilizing functional group and at least one amino substituent; and at least one oil carrier.

The present invention also relates to methods of treating, caring for and/or making up keratinous material (for example, skin, hair, eyes, eyelashes, lips or hair) by applying the compositions of the present invention to the keratinous material in an amount sufficient to treat, care for and/or make up the keratinous material.

The present invention also relates to compositions containing at least one polar modified polymer; at least one alkoxysilane having at least one solubilizing functional group and at least one amino substituent; at least one oil carrier; optionally, water; optionally, at least one desired agent; and optionally, at least one auxiliary agent.

The present invention also relates to compositions as described above which impart good adhesion, long-wear and/or transfer-resistance properties, as well as improved feel or texture properties to a composition, such as a cosmetic composition, upon application to a surface or a keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Transfer resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

"Long wear" compositions as used herein, refers to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

"Waterproof" as used herein refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100 degrees C.

"Non-volatile", as used herein, means having a flash point of greater than about 100 degrees C.

The compositions and methods of the present invention can comprise, consist of, or consist essentially of the essential elements and limitations of the invention described herein, as well as any additional or optional ingredients, components, or limitations described herein or otherwise useful.

Polar Modified Polymer

According to the present invention, compositions comprising at least one polar modified polymer are provided. "Polar modified polymer" as used herein refers to "oil-soluble polar modified polymers" and/or "oil-soluble high carbon polar modified polymers."

Oil-Soluble Polar Modified Polymer

According to the present invention, compositions comprising at least one oil-soluble polar modified polymer are provided. "Polar modified polymer" as used herein refers to a hydrophobic homopolymer or copolymer which has been modified with hydrophilic unit(s). "Oil-soluble" as used herein means that the polar modified polymer is soluble in oil.

Suitable monomers for the hydrophobic homopolymers and/or copolymers include, but are not limited to, cyclic, linear or branched, substituted or unsubstituted, C2-C20 compounds such as, for example, styrene, ethylene, propylene, isopropylene, butylene, isobutylene, pentene, isopentene, isoprene, hexene, isohexene, decease, isodecene, and octadecene, including all ranges and subranges therebetween. Preferably, the monomers are C2-C8 compounds, more preferably C2-C6 compounds, and most preferably C2-C4 compounds such as ethylene, propylene and butylenes.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to the present invention, the polar modified polymer is oil-soluble: that is, the polymer does not contain a sufficient amount of hydrophilic unit(s) to render the entire polymer water-soluble or oil-insoluble. According to preferred embodiments, the polar modified polymer contains the same amount of hydrophobic monomer as hydrophilic unit (1:1 ratio) or more hydrophobic monomer than hydrophilic unit. According to particularly preferred embodiments, the polar modified polymer contains 50% or less hydrophilic unit(s) (based on weight of the polymer), 40% or less hydrophilic unit(s), 30% or less hydrophilic unit(s), 20% or less hydrophilic unit(s), 10% or less hydrophilic unit(s), 5% or less hydrophilic unit(s), 4% or less hydrophilic unit(s), or 3% or less hydrophilic unit(s).

Preferably, the polar modified polymer has from about 0.5% to about 10% hydrophilic units, more preferably from about 1% to about 8% hydrophilic units by weight with respect to the weight of the polymer, including all ranges and subranges therebetween. Particularly preferred hydrophilically modified polymers are ethylene and/or propylene homopolymers and copolymers which have been modified with maleic anhydride units.

According to preferred embodiments of the present invention, the polar modified polymer is a wax. According to particularly preferred embodiments, the polar modified wax is made via metallocene catalysis, and includes polar groups or units as well as a hydrophobic backbone. Suitable modified waxes include those disclosed in U.S. patent application publication no. 20070031361, the entire contents of which is hereby incorporated by reference. Particularly preferred polar modified waxes are C2-C3 polar modified waxes.

In accordance with preferred embodiments of the present invention, the polar modified wax is based upon a homopolymer and/or copolymer wax of hydrophobic monomers and has a weight-average molecular weight Mw of less than or equal to 25 000 g/mol, preferably of 1000 to 22 000 g/mol and particularly preferably of 4000 to 20,000 g/mol, a number-average molecular weight Mn of less than or equal to 15 000 g/mol, preferably of 500 to 12 000 g/mol and particularly preferably of 1000 to 5000 g/mol, a molar mass distribution Mw/Mn in the range from 1.5 to 10, preferably from 1.5 to 5, particularly preferably from 1.5 to 3 and especially preferably from 2 to 2.5, which have been obtained by metallocene catalysis. Also, the polar modified wax preferably has a melting point above 75° C., more preferably above 90° C. such as, for example, a melting point between 90° C. and 160° C., preferably between 100° C. and 150° C., including all ranges and subranges therebetween.

In the case of a copolymer wax, it is preferable to have, based on the total weight of the copolymer backbone, 0.1 to 30% by weight of structural units originating from the one monomer and 70.0 to 99.9% by weight of structural units originating from the other monomer. Such homopolymer and copolymer waxes can be made, for example, by the process described in EP 571 882, the entire contents of which is hereby incorporated by reference, using the metallocene catalysts specified therein. Suitable preparation processes include, for example, suspension polymerization, solution polymerization and gas-phase polymerization of olefins in the presence of metallocene catalysts, with polymerization in the monomers also being possible.

Polar modified waxes can be produced in a known manner from the hompopolymers and copolymers described above by oxidation with oxygen-containing gases, for example air, or by graft reaction with polar monomers, for example maleic acid or acrylic acid or derivatives of these acids. The polar modification of metallocene polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable polar modified waxes include, but are not limited to, homopolymers and/or copolymers of ethylene and/or propylene groups which have been modified with hydrophilic units such as, for example, maleic anhydride, acrylate, methacrylate, polyvinylpyrrolidone (PVP), etc. Preferably, the polar modified wax has from about 0.5% to about 10% hydrophilic units, more preferably from about 1% to about 8% hydrophilic units by weight with respect to the weight of the wax, including all ranges and subranges therebetween. Particularly preferred hydrophilically modified waxes are ethylene and/or propylene homopolymers and copolymers which have been modified with maleic anhydride units.

Particularly preferred polar modified waxes for use in the present invention are C2-C3 polar modified waxes such as polypropylene and/or polyethylene-maleic anhydride modified waxes ("PEMA," "PPMA," "PEPPMA") commercially available from Clariant under the trade name LICOCARE or LICOCENE, Specific examples of such waxes include products marketed by Clariant under the LicoCare name having designations such as PP207.

Other suitable polar modified polymers include, but are not limited to A-C 573 A (ETHYLENE-MALEIC ANHYDRIDE COPOLYMER; Drop Point, Mettler: 106° C.) from Honeywell, A-C 596 A (PROPYLENE-MALEIC ANHYDRIDE COPOLYMER; Drop Point, Mettler: 143° C.) from Honeywell, A-C 597 (PROPYLENE-MALEIC ANHYDRIDE COPOLYMER; Drop Point, Mettler: 141° C.) from Honeywell, ZeMac®, copolymers (from VERTELLUS) which are 1:1 copolymers of ethylene and maleic anhydride, polyisobutylene-maleic anhydride sold under the trade name ISOBAM (from Kuraray), polyisoprene-graft-maleic anhydride sold by Sigma Aldrich, poly(maleic anhydride-octadecene) sold by Chevron Philips Chemical Co., poly(ethylene-co-butyl acrylate-co-maleic anhydride) sold under the trade name of Lotader (e.g. 2210, 3210, 4210, and 3410 grades) by Arkema, copolymers in which the butyl acrylate is replaced by other alkyl acrylates (including methyl acrylate [grades 3430, 4404, and 4503] and ethyl acrylate [grades 6200, 8200, 3300, TX 8030, 7500, 5500, 4700, and 4720) also sold by Arkema under the Lotader name, and isobutylene maleic anhydride copolymer sold under the name ACO-5013 by ISP.

Oil-Soluble High Carbon Polar Modified Polymer

According to the present invention, compositions comprising at least one oil-soluble high carbon polar modified polymer are also provided. "Polar modified polymer" as used herein refers to a hydrophobic homopolymer or copolymer which has been modified with hydrophilic unit(s). "Oil-soluble" as used herein means that the polar modified polymer is soluble in oil. "High carbon" means more than 20 carbon atoms.

Suitable monomers for the hydrophobic homopolymers and/or copolymers include, but are not limited to, cyclic, linear or branched, substituted or unsubstituted, C22-C40 compounds such as, C22-C28 compounds, C24-C26 compounds, C26-C28 compounds, and C30-C38 compounds, including all ranges and subranges therebetween. Preferably, the monomers are C24-26 compounds, C26-C28 compounds or C30-C38 compounds.

Suitable hydrophilic unit(s) include, but are not limited to, maleic anhydride, acrylates, alkyl acrylates such as, for example, methyl acrylate, ethyl acrylate, propyl acrylate, and butyl acrylate, and polyvinylpyrrolidone (PVP).

According to preferred embodiments, the oil-soluble high carbon polar modified polymer is a wax. Also preferably, the oil-soluble high carbon polar modified polymer wax has one or more of the following properties:

a weight-average molecular weight Mw of less than or equal to 30 000 g/mol, preferably of 500 to 10 000 g/mol and particularly preferably of 1000 to 5,000 g/mol, including all ranges and subranges therebetween;

a number-average molecular weight Mn of less than or equal to 15 000 g/mol, preferably of 500 to 12 000 g/mol and particularly preferably of 1000 to 5000 g/mol, including all ranges and subranges therebetween;

a molar mass distribution Mw/Mn in the range from 1.5 to 10, preferably from 1.5 to 5, particularly preferably from 1.5 to 3 and especially preferably from 2 to 2.5, including all ranges and subranges therebetween; and/or a crystallinity of 8% to 60%, preferably 9% to 40%, and more preferably 10% to 30%, including all ranges and subranges therebetween, as determined by differential scanning calorimetry.

According to preferred embodiments relating to a copolymer wax, it is preferable to have, based on the total weight of the copolymer backbone, 0.1 to 30% by weight of structural units originating from the one monomer and 70.0 to 99.9% by weight of structural units originating from the other monomer.

Waxes of the present invention can be based upon homopolymers or copolymers made, for example, by the process described in EP 571 882, the entire contents of which is hereby incorporated by reference. Suitable preparation processes include, for example, suspension polymerization, solution polymerization and gas-phase polymerization of olefins in the presence of catalysts, with polymerization in the monomers also being possible.

Oil-soluble high carbon polar modified polymer wax can be produced in a known manner from the hompopolymers and copolymers described above by oxidation with oxygen-containing gases, for example air, or by graft reaction with polar monomers, for example maleic acid or acrylic acid or derivatives of these acids. The polar modification of polyolefin waxes by oxidation with air is described, for example, in EP 0 890 583 A1, and the modification by grafting is described, for example, in U.S. Pat. No. 5,998,547, the entire contents of both of which are hereby incorporated by reference in their entirety.

Acceptable oil-soluble high carbon polar modified polymer waxes include, but are not limited to, homopolymers and/or copolymers of C24, C25 and/or C26 groups, copolymers C26, C27 and/or C28 groups, or copolymers of C30-C38 groups, which have been modified with hydrophilic units such as, for example, maleic anhydride, acrylate, methacrylate, polyvinylpyrrolidone (PVP), etc. Preferably, the oil-soluble high carbon polar modified polymer wax has from about 5% to about 30% hydrophilic units, more preferably from about 10% to about 25% hydrophilic units by weight with respect to the weight of the wax, including all ranges and subranges therebetween. Particularly preferred hydrophilically modified waxes are C26, C27 and/or C28 homopolymers and copolymers which have been modified with maleic anhydride units.

Particularly preferred oil-soluble high carbon polar modified polymer waxes for use in the present invention are C26-C28 alpha olefin maleic acid anhydride copolymer waxes commercially available from Clariant under the trade name LICOCARE or LICOCENE. Specific examples of such waxes include products marketed by Clariant under the Lico-Care name having designations such as CM 401, which is a maleic anhydride modified wax having a Mw of 2025 and a crystallinilty of 11%. C30-C38 olefin/isopropylmaleate/maleic anhydride copolymer sold by Baker Hughes under the name Performa® V 1608, and C24-C26 alpha olefin acrylate copolymer wax commercially available from Clariant under the trade name LICOCARE CA301 LP3346 based on a polar backbone with C24-26 side chains with alternating ester and carboxylic acid groups.

According to other embodiments of the present invention, the polar modified polymer is not a wax. In accordance with these embodiments of the present invention, the polar modified polymer is based upon a homopolymer and/or copolymer of hydrophobic monomer(s) and has a weight-average molecular weight Mw of less than or equal to 1,000,000 g/mol, preferably of 1000 to 250,000 g/mol and particularly preferably of 5,000 to 50,000 g/mol, including all ranges and subranges therebetween.

In accordance with these embodiments, the polar modified polymer can be of any form typically associated with polymers such as, for example, block copolymer, a grafted copolymer or an alternating copolymer. For example, the polar modified polymer can contain a hydrophobic backbone (such as polypropylene and/or polyethylene) onto which hydrophilic groups (such as maleic anhydride) have been attached by any means including, for example, grafting. The attached groups can have any orienation (for example, atactic, isotactic or syndiotactic along the backbone).

Preferably, the polar modified polymer(s) of the present invention represent from about 1% to about 30% by weight, more preferably from about 3% to about 25% by weight, and most preferably from about 5% to about 20% by weight, of the total weight of the composition, including all ranges and subranges therebetween.

Alkoxysilane

In accordance with the present invention, the alkoxysilane having at least one solubilizing functional group and an amino substituent has an amine group available to react with hydrophilic groups on the backbone of the polar modified polymer.

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups for use in accordance with the present disclosure include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane present in the composition comprises at least one solubilizing functional group, which may be identical or different, such as those previously defined.

The at least one alkoxysilane having at least one solubilizing functional group and amino substituent present in the composition of the present disclosure may comprise at least one silicon atom, for example, one silicon atom.

The at least one alkoxysilane having at least one solubilizing functional group and amino substituent present in the composition may, in at least one embodiment, comprise two or three alkoxy functions. In another embodiment, the alkoxy functional groups are chosen from methoxy and ethoxy functional groups.

According to one embodiment, the at least one alkoxysilane having at least one solubilizing functional group and amino substituent present in the composition of the present disclosure is chosen from compounds of formula (I):

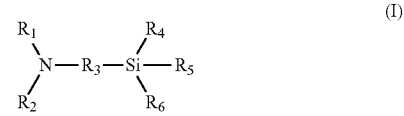

wherein:
$R_4$ is chosen from OR' groups;
$R_5$ is chosen from OR" groups;
$R_6$ is chosen from OR'" groups;
$R_1$, $R_2$ are chosen from hydrogen;
$R_3$, R', R", R'", which may be identical or different, are chosen from linear and branched, saturated and unsaturated hydrocarbon groups, optionally bearing at least one additional chemical group, wherein R', R", and R'" may also be chosen from hydrogen.

In at least one embodiment, the R', R", and R'" groups are chosen from $C_1$-$C_{12}$ alkyl, $C_6$-$C_{14}$ aryl, $C_1$-$C_8$ alkyl-$C_6$-$C_{14}$ aryl, and $C_6$-$C_{14}$ aryl-$C_1$-$C_8$-alkyl radicals.

Particularly preferred alkoxysilanes having at least one solubilizing functional group and at least one amino substituent include alkoxysilanes comprising a silicone atom. Suitable examples include those of formula R(4-n)SiXn, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

In another embodiment, the useful alkoxysilanes of the present invention may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:

3-(m-aminophenoxy)propyltrimethoxysilane, of the formula:

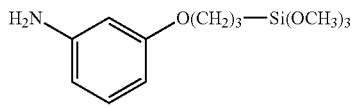

provided by GELEST,
p-aminophenyltrimethoxysilane, of formula:

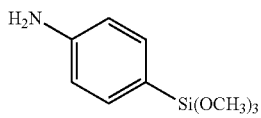

provided by GELEST, and
N-(2-aminoethylaminomethyl)phenethyltrimethoxysilane, of the formula:

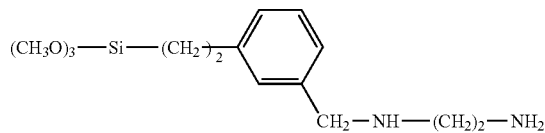

provided by GELEST.

In another embodiment the at least one alkoxysilane having at least one solubilizing functional group and at least one amino substituent is a trialkoxysilane.

In a preferred embodiment, the at least one alkoxysilane having at least one solubilizing functional group and at least one amino substituent present in the composition of the present disclosure is a γ-aminopropyltriethoxysilane, also known as 3-aminopropyltriethoxysilane.

The at least one alkoxysilane having at least one solubilizing functional group and at least one amino substituent of the present invention is soluble in both oil and water.

The at least one alkoxysilane having at least one solubilizing functional group and at least one amino substituent is employed in the composition of the invention in an amount ranging from about 0.01 to about 10% by weight, such as from about 0.01 to about 5%, such as from about 0.05 to about 3% by weight, and from about 0.1 to about 2% by weight, based on the total weight of the composition, including all ranges and subranges therebetween.

Reaction Product

Although not wanting to be bound by any particular theory, it is believed that the polar modified polymer reacts with the alkoxysilane having at least one solubilizing functional group and at least one amino substituent to form links or bonds between the amine groups of the alkoxysilane and the hydrophilic groups of the polar modified polymer. The appropriate amount of the alkoxysilane having at least one solubilizing functional group and at least one amino substituent to react with the polar modified polymer to obtain a reaction product can be easily determined, taking into account the number/amount of reactive amine groups on the alkoxysilane having at least one solubilizing functional group and at least one amino substituent and the number/amount of corresponding reactive groups on the polar modified polymer (for example, maleic anhydride groups). According to preferred embodiments, excess polar modified polymer (as determined by the relative number/amount of corresponding reactive groups on the polymer as compared to the reactive amine group(s) on the alkoxysilane) is reacted with the alkoxysilane having at least one solubilizing functional group and at least one amino substituent. The molar ratio of the alkoxysilane having at least one solubilizing functional group and at least one amino substituent to polar modified polymer may range from between 0.003 and 6, such as between 0.01 and 1.5, and such as between 0.1 and 0.5, including all ranges and subranges therebetween.

According to the present invention, any suitable amine chemistry can be used to form the reaction product of the present invention. The exact chemistry will depend upon the nature of the corresponding reactive group of the polar modified polymer with which the amine groups of the alkoxysilane having at least one solubilizing functional group and at least one amino substituent will react. However, once the nature of the corresponding reactive groups is known, their reaction with the amine groups will proceed according to known amine chemistry principles.

According to preferred embodiments, the polar modified polymer is initially present in an oil carrier, and the alkoxysilane having at least one solubilizing functional group and at least one amino substituent is blended into the oil carrier during production of the compositions of the present invention. Because the polar modified polymer is typically solid at room temperature, the oil carrier containing the polar modified polymer is preferably heated to liquefy the wax prior to combination with the alkoxysilane having at least one solubilizing functional group and at least one amino substituent. Preferably, the oil carrier is heated beyond the melting point of the polar modified polymer, typically up to about 70° C., 80° C., 90° C., 100° C. or 110° C. Then, the polar modified polymer is preferably combined with the alkoxysilane having at least one solubilizing functional group and at least one amino substituent through blending at room temperature or at an elevated temperature (that is, at a temperature between room temperature and the temperature at which the polar modified wax was liquefied or melted or at a higher temperature) such as, for example, about 30° C., 40° C., 50° C., 60° C., 70° C., 80° C., 90° C., 120° C. or above 120° C. for at least about 1 minute, preferably at least about 5 minutes, preferably at least about 30 minutes, including all time intervals therein.

According to preferred embodiments of the present invention, the combination of the polar modified polymer and the alkoxysilane having at least one solubilizing functional group and at least one amino substituent in one or more oil carriers can comprise an anhydrous composition. Preferably, the molar ratio of the alkoxysilane having at least one solubilizing functional group and at least one amino substituent to polar modified polymer in an anhydrous composition may range from between 0.003 and 1, preferably from between 0.01 and 0.6, and preferably from between 0.1 and 0.4, including all ranges and subranges therebetween.

According to other preferred embodiments of the present invention, the alkoxysilane having at least one solubilizing functional group and at least one amino substituent is initially present in a water carrier in which the alkoxysilane undergoes hydrolysis and condensation to form a polyamine. The polar modified polymer is then combined with the alkoxysilane which is now in the form of a polyamine by combining the polar modified polymer's oil carrier and the alkoxysilane's water carrier. Although not wanting to be bound by any particular theory, it is believed that an emulsion constituting an oil phase and a water phase is thus formed from the combination of the oil carrier and the water carrier and that a reaction between the polar modified polymer and the amino group(s) on the alkoxysilane can occur at the oil-water interface of the emulsion.

According to another preferred embodiment of the present invention, the polar modified polymer is initially present in an oil carrier and the alkoxysilane having at least one solubilizing functional group and at least one amino substituent is initially present with both the polar modified polymer in the oil carrier and in a separate water carrier. Although not wanting to be bound to any particular theory, it is believed in this case, that the polar modified polymer will first react with the alkoxysilane having at least one solubilizing functional group and at least one amino substituent present in the oil carrier after which any unreacted hydrophilic groups on the polar modified polymer can then react with the amino group(s) of the condensation product of the alkoxysilane present in the water phase and/or with the ethoxy groups on the alkoxysilane in the oil carrier with any free hydroxyl groups on the alkoxysilane in the water carrier at the oil-water interface of the emulsion formed between the oil carrier and the water carrier. Preferably, the molar ratio of the alkoxysilane having at least one solubilizing functional group and at least one amino substituent to polar modified polymer in an emulsion composition may range from between 0.003 and 6, preferably from between 0.01 and 3.5, and preferably from between 0.1 and 0.5, including all ranges and subranges therebetween.

According to other embodiments, the polar modified polymer and the alkoxysilane having at least one solubilizing functional group and at least one amino substituent can be added to the oil carrier first, and then the water can be subsequently added to the mixture to form an emulsion. Preferably, the molar ratio of the alkoxysilane having at least one solubilizing functional group and at least one amino substituent to polar modified polymer is between 0.003 and 0.15, preferably between 0.005 and 0.13, and preferably between 0.01 and 0.05, including all ranges and subranges therebetween.

Without intending to be bound by any particular theory, it is believed that due to the chemical and physical reactions which take place when the polar modified polymer is combined with the alkoxysilane having at least one solubilizing functional group and at least one amino substituent, the subsequent reaction product or composition that is formed is surprisingly and unexpectedly able to entrap large amounts of water molecules within its hydrophobic matrix. The resultant product or composition resulting from the chemical and physical reactions between the polar modified polymer and the alkoxysilane having at least one solubilizing functional group and at least one amino substituent is capable of forming a film, is self-emulsifying, and transfer-resistant. Moreover, the product or composition is both stable and capable of carrying various types of ingredients.

According to preferred embodiments, the oil carrier comprises volatile and/or non-volatile oils. Such oils can be any acceptable oil including but not limited to silicone oils and/or hydrocarbon oils.

According to preferred embodiments, the oil carrier comprises one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the oil carrier comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |

TABLE 2-continued

| Compound | Flash Point (° C.) |
|---|---|
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to preferred embodiments of the present invention, the oil carrier comprises at least one non-volatile oil. Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The oil carrier of the present invention is employed in the composition of the invention in an amount ranging from about 1 to about 90% by weight, more preferably from about 10% to about 85%, and more preferably from about 40% to about 80% by weight, based on the total weight of the composition, including all ranges and subranges therebetween.

According to preferred embodiments of the present invention, the oil carrier, the water carrier, or both comprise a desired agent to be incorporated within the reaction product or the compositions of the present invention. The desired agent can be, for example, any colorant (pigment, dye, etc.), any pharmaceutically or cosmetically active agent, or any film forming agent known in the art. Such a desired agent can be incorporated into the reaction product or into the compositions of the present invention. When the desired agent is incorporated into the reaction product, it can be active during subsequent use of a composition comprising the reaction product. For example, a cosmetic makeup composition or a paint composition comprising colorants within the reaction product can provide colorant and/or film forming agent to a substrate (skin, lips, wall, frame, etc.) during use to provide the substrate with the desired film and/or color. Similarly, a pharmaceutical or cosmetic composition comprising a pharmaceutically active agent or a skin active agent can provide such active agent to the patient or consumer upon use (for example, a transdermal patch containing the reaction product of the present invention within which is a pharmaceutically or cosmetically active agent, or a tablet or capsule containing the same reaction product/active agent combination).

Acceptable colorants include pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

Representative nacreous pigments include white nacreous pigments such as mica coated with titanium or with bismuth oxychloride, colored nacreous pigments such as titanium mica with iron oxides, titanium, mica with ferric blue or chromium oxide, titanium mica with an organic pigment chosen from those mentioned above, and nacreous pigments based on bismuth oxychloride.

Representative pigments include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium.

Representative cosmetically active agents include, but are not limited to agents for combating free radicals, UV screening agents, moisturizing agents, and humectants. In the event that water or an aqueous carrier is employed in the composition of the present invention, suitable examples of moisturizing agents are, but not limited to, polyols such as glycerin and glycosaminoglycans (GAGs). GAgS are also referred to as acidic mucopolysaccharides on account of their high water-retaining capacity, their carbohydrate nature and their acidic nature derived from the numerous negative charges thereon. The strong anionic nature of GAGs is explained by the presence of carboxylate groups.

Suitable examples of glycosaminoglycans are hyaluronic acid or hyaluronan (HA), heparan sulfate (HS), heparin (HP), chondroitin, chondroitin sulfate (CS), chondroitin 4-sulfate or chondroitin sulfate A (CSA), chondroitin 6-sulfate or chondroitin sulfate C (CSC), dermatan sulfate or chondroitin sulfate B (CSB) and keratan sulfate (KS).

In one preferred embodiment of the present invention, the glycosaminoglycan is chosen from hyaluronic acid, its derivatives and its salts. In the context of the present invention, the term "hyaluronic acid or a derivative thereof/" covers the basic unit of hyaluronic acid which includes the smallest fraction of hyaluronic acid comprising a disaccharide dimer, namely D-glucuronic acid and N-acetylglucosamine.

The term "hyaluronic acid or a derivative thereof" also comprises, in the context of the present invention, the linear polymer comprising the polymeric unit described above, linked together in the chain via alternating beta(1,4) and beta(1,3) glycosidic linkages, having a molecular weight (MW) that can range between 380 and 13,000,000 daltons (Da). This molecular weight depends in large part on the source from which the hyaluronic acid is obtained and/or on the preparation methods.

The term "hyaluronic acid or a derivative thereof" also comprises, in the context of the present invention, the hyaluronic acid salts, and in particular the alkali metals salts such as the sodium salt and the potassium salt.

In the natural state, hyaluronic acid is present in pericellular gels, in the base substance of the connective tissues of vertebrate organs such as the dermis and epithelial tissues, and in particular in the epidermis, in the synovial fluid of the joints, in the vitreous humor, in the human umbilical cord and in the crista galli apophysis.

Thus, the term "hyaluronic acid or a derivative thereof" comprises all the fractions or subunits of hyaluronic acid having a molecular weight in particular within the molecular weight range recalled above.

According to a preferred embodiment of the invention the hyaluronic acid fractions suitable for the use covered by the present invention have a molecular weight of between 50,000 and 5,000,000, in particular between 100,000 and 5,000,000, especially between 400,000 and 5,000,000 Da. In this case, the term used is high-molecular-weight hyaluronic acid.

Alternatively, the hyaluronic acid fractions that may also be suitable for the use in the present invention are chosen from those with a molecular weight of between 50,000 and 400,000 Da (intermediate-molecular-weight hyaluronic acid) and from those with a molecular weight of less than 50,000 Da (low-molecular-weight hyaluronic acid).

Finally, the term "hyaluronic acid or a derivative thereof" also comprises hyaluronic acid esters in particular those in which all or some of the carboxylic groups of the acid functions are esterified with oxyethylenated alkyls or alcohols, containing from 1 to 20 carbon atoms, in particular with a degree of substitution at the level of the D-glucuronic acid of the hyaluronic acid ranging from 0.5 to 50 percent. Mention may in particular be made of methyl, ethyl, n-propyl, n-pentyl, benzyl and dodecyl esters of hyaluronic acid.

The molecular weights indicated above are also valid for the hyaluronic acid esters.

Hyaluronic acid may in particular be hyaluronic acid supplied by the company Hyactive under the trade name CPN (MW: 10 to 150 kDa), by the company Soliance under the trade name Cristalhyal (MW: 1.1 million Da), by the company Bioland under the name Nutra HA (MW: 820,000 Da), by the company Bioland under the name Nutra AF (MW: 69,000 Da, by the company Bioland under the name Oligo HA (MW: 6100 Da) or else by the company Vam Farmacos Metica under the name D Factor (MW: 380 Da).

In one embodiment, the hyaluronic acid is present in the form of spheres. In particular, such spheres are sold by the company BASF under the name Sphere d'Acide Hyaluronique [hyaluronic acid sphere]. It is a mixture of hyaluronic acid of various molecular weights, i.e. of MW 1.5 million, 400,000 and 600,000 Da.

The preferred form of hyaluronic acid in the present invention is sodium hyaluronate, which is commercially available from Soliance in three different forms produced from the fermentation of lactic bacteria on a plant substrate and known under the tradenames Bashyal, Vitalhyal and Cristalhyal, whose molecular weights range from less than 0.2 million Da to more than 1 million Da.

Preferably, hyaluronic acid is employed in the reaction product and in the compositions of the present invention in an amount of from about 0.01% to about 5% by weight, more preferably, from about 0.2% to about 2.0% by weight, and more preferably, from about 0.5% to about 1.5% by weight with respect to the total weight of the reaction product/composition, including all ranges and subranges therebetween.

Acceptable film forming agents and/or rheological agents are known in the art and include, but are not limited to, those disclosed in U.S. patent application publication no. 2004/0170586, the entire contents of which is hereby incorporated by reference.

Non-limiting representative examples of acceptable film forming/rheolgocial agents include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from aqueous polyurethane dispersions, vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film forming/rheological agents also include water soluble polymers such as, for example, high molecular weight crosslinked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropyltrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, polyethylene oxide) based thickeners, sodium carbomer, and mixtures thereof.

Compositions of the present invention can optionally further comprise any additive or auxiliary agents usually used in the field(s) under consideration. For example, dispersants such as poly(12-hydroxystearic acid), antioxidants, essential oils, sunscreens, preserving agents, fragrances, fillers, neutralizing agents, pH adjusters, cosmetic and dermatological active agents such as, for example, emollients, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which are hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

In the event that water is employed in the composition of the present invention, an embodiment of the composition of the present invention may include an auxiliary ingredient chosen from at least one surfactant. The surfactant may be chosen from anionic, nonionic, amphoteric, cationic, and zwitterionic surfactants.

Preferably, the at least one surfactant may be employed in the compositions of the present invention in an amount of from about 0.1% to about 10% by weight, more preferably, from about 1% to about 7.5% by weight, and more preferably, from about 1.5% to about 5% by weight with respect to the total weight of the composition, including all ranges and subranges therebetween.

In the event that the composition of the present invention includes water, the composition may comprise water in an amount of from about 1% to about 75% water, more preferably from about 5% to about 65% water, and more preferably from about 15% to about 50% water by weight with respect to the total weight of the composition, including all ranges and subranges therebetween.

According to other preferred embodiments, compositions of the present invention comprising water can include compositions in the form of a solid, a semi-solid or a cream such as a lipstick or a stick foundation or a cream foundation. Such compositions can comprise from between about 5 to about 65%, preferably from about 10 to about 50%, more preferably from about 15 to about 25% water by weight with respect to the total weight of the composition, including all ranges and subranges therebetween.

In one preferred embodiment of the present invention, the compositions of the present invention are substantially free of silicone oils (i.e., contain less than about 0.5% silicone oils). In another embodiment, the compositions are substantially free of non-silicone oils (i.e., contain less than about 0.5% non-silicone oils). In another embodiment, the compositions are substantially free of non-volatile oils (i.e., contain less than about 0.5% non-volatile oils).

Another preferred embodiment of the present invention is an emulsion which is substantially free of surfactant (that is, less than 3% of surfactant), essentially free of surfactant (that is, less than 2% surfactant), or free of surfactant (that is, less than 0.5% surfactant).

Another particularly preferred embodiment of the present invention is a composition which contains so little elastomer that the presence of such an elastomer does not affect the cosmetic properties of the composition. Preferably, the compositions are substantially free of such elastomers (i.e., contain less than about 0.5% elastomer), essentially free of such elastomers (i.e., contain less than about 0.25% elastomer) or free of such elastomer (i.e., contain no elastomer).

According to some embodiments of the present invention, the compositions of the present invention are anhydrous. By "anhydrous," it is meant that the composition contains substantially no water (that is, less than about 5% by weight of the composition of water).

According to other embodiments of the present invention, the composition is an emulsion wherein the alkoxysilane having at least one solubilizing functional group and at least one amino substituent is present in the water or an aqueous carrier or in both the oil carrier and in the water or aqueous carrier.

Compositions of the present invention may further comprise a desired agent such as a cosmetically active agent chosen from colorants.

In some embodiments, when water is present in the composition of the present invention, hyaluronic acid is additionally present in the water or aqueous carrier. In other embodiments, a surfactant is additionally present in the water or aqueous carrier.

According to other preferred embodiments, cosmetic and personal care compositions and methods of treating, caring for and/or making up or enhancing the appearance of keratinous material by applying such compositions to the keratinous material in an amount sufficient to treat, care for and/or enhance the appearance of the keratinous material are provided. In accordance with these preceding preferred embodiments, the compositions of the present invention comprising at least one polar modified polymer and at least one alkoxysilane having at least one solubilizing functional group and at least one amino substituent are applied topically to the desired area of the keratin material in an amount sufficient to treat, care for and/or enhance the appearance of the keratinous material. The compositions may be applied to the desired area as needed, preferably once or twice daily, more preferably once daily and then preferably allowed to dry before subjecting to contact such as with clothing or other objects (for example, a glass or a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to a preferred embodiment of the present invention, compositions having improved cosmetic properties such as, for example, improved waterproof characteristics, improved feel upon application (for example, texture, reduced drag or tackiness), increased anti-smudging properties, shine/color characteristics and/or increased long wear properties are provided.

In some embodiments of the present invention, depending on the levels of the alkoxysilane having at least one solubilizing functional group and at least one amino substituent and/or of the polar modified polymer, compositions with varying viscosity and texture characteristics such as a unique bouncy gel texture or a creamy texture or a soft and smooth texture are provided.

According to other embodiments of the present invention, methods of improving the anti-smudging, waterproof, transfer-resistance and/or long wear properties of a composition, comprising adding at least one polar modified polymer and at least one alkoxysilane having at least one solubilizing functional group and at least one amino substituent to the composition are provided. In accordance with this embodiment, the at least one polar modified polymer and the at least one alkoxysilane having at least one solubilizing functional group and at least one amino substituent are present in amounts sufficient to achieve the desired result.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Anhydrous Compositions (1-3)

| Phase | Chemical Name | Comparative Example 1 | Inventive Example 2 | Inventive Example 3 |
|---|---|---|---|---|
| A1 | Isododecane | QS | QS | QS |
| A1 | Octododecanyl Pentanoate | 20 | 20 | 20 |
| A1 | Polyalkylene/Maleic Anhydride Copolymer* (PPMA) | 20 | 20 | 20 |
| A2 | Aminopropyl Triethoxysilane (APTES) | 0 | 0.5 | 1 |
| | TOTAL | 100 | 100 | 100 |

*PP207 is a linear polypropylene-ethylene-maleic anhydride copolymer wax commercially available from Clariant under the tradename LICOCARE PP207 LP 3349.

Procedure

For each composition, all ingredients in Phase A1 were added to a suitable size metal container. The contents were heated to 85 Celsius degrees or until all solids had melted.

All ingredients indicated in phase A2 were added to the metal container in a drop-wise fashion.

Contents were mixed at 80-85 Celsius degrees for 1 hour.

Contents were cooled to 25 Celsius degree while mixing.

Comparative Example 1 contained Polyalkylene/Maleic Anhydride Copolymer (PPMA, PP207) as the polar modified polymer (control). Inventive Examples 2 and 3 contained PPMA and aminopropyl triethoxysilane (APTES) as the alkoxysilane having at least one solubilizing functional group and amino substituent with an amine group.

Comparing with the control (Comparative Example 1), it was found that Inventive Example 2 (PPMA+APTES) formed a viscous liquid that had a high affinity to keratinous substrates. By increasing the concentration of APTES (Inventive Example 3), a bouncy gel was formed. With the viscous liquid, the film was easily spreadable and shiny, while the bouncy gel provided a unique texture.

Emulsion Compositions: PPMA in Oil Phase and APTES in Water Phase

Example 4-6

| Phase | Chemical Name | Comparative Example 4 | Inventive Example 5 | Inventive Example 6 |
|---|---|---|---|---|
| A | Isododecane | QS | QS | QS |
| A | Octododecanyl Pentanoate | 20 | 20 | 20 |
| A | Polyalkylene/Maleic Anhydride Copolymer* (PPMA) | 20 | 20 | 20 |
| B | Water | 25 | 25 | 25 |
| B | Aminopropyl Triethoxysilane (APTES) | 0 | 0.25 | 1 |
| | TOTAL | 100 | 100 | 100 |

*PP207 is a linear polypropylene-ethylene-maleic anhydride copolymer wax commercially available from Clariant under the tradename LICOCARE PP207 LP 3349.

Procedure

For each composition, all ingredients in Phase A were added to a suitable size metal container. The contents were heated to 85 Celsius degrees or until all solids had melted.

All ingredients indicated in phase B were added to a suitable size side container B, and mixed until uniform. The contents were also heated to 85 Celsius degrees.

When both containers were at their proper temperatures, side container B was slowly added to main container A while mixing at high speed.

Contents were mixed at 80-85 Celsius degrees for 1 hour. Contents were cooled to 25 Celsius degrees while mixing.

Comparative Example 4 contained PPMA and distilled water (control). Invention Examples 5 and 6 contained PPMA, and APTES in water.

Comparing with the control (Comparative Example 4), it was found that Inventive Example 5 (PPMA+Water+APTES) formed a cream that had a high affinity to keratinous substrates and did not undergo phase separation. By increasing the concentration of APTES (Inventive Example 6), a bouncy gel with high affinity to keratinous substrates was formed. While the cream provided a film that was easily spreadable on keratinous substrates, and was smooth, soft and shiny, the bouncy gel provided a unique texture. Increasing the APTES concentration also caused the emulsion droplet size to decrease, as observed by optical microscopy.

Emulsion Compositions with Sodium Hyaluronate: PPMA in Oil Phase and APTES+HA in Water Phase Examples 7-10

| Phase | Chemical Name | Inventive Example 7 | Inventive Example 8 | Inventive Example 9 | Inventive Example 10 |
|---|---|---|---|---|---|
| A | Polyalkylene/Maleic Anhydride Copolymer* (PPMA) | 7.00 | 7.00 | 7.00 | 7.00 |
| A | Isododecane | 43.00 | 43.00 | 43.00 | 43.00 |
| B | Water | QS | QS | QS | QS |
| B | Sodium Hyaluronate (HA) | 0.50 | 0.50 | 0.50 | 0.50 |
| B | Aminopropyl Triethoxysilane (APTES) | 0.58 | 1.67 | 3.33 | 6.67 |

*PP207 is a linear polypropylene-ethylene-maleic anhydride copolymer wax commercially available from Clariant under the tradename LICOCARE PP207 LP 3349.

Procedure

For each composition, all ingredients in Phase A were added to a suitable size metal container. The contents were heated to 85 Celsius degrees or until all solids had melted.

All ingredients indicated in phase B were added to a suitable size side container B, and mixed until uniform. The contents were also heated to 85 Celsius degrees for 8 hrs.

When both containers were at their proper temperatures, side container B was slowly added to main container A while mixing at high speed.

Contents were mixed at 80-85 Celsius degrees for 1 hour. Contents were cooled to 25 Celsius degree while mixing.

Example 7 was a light cream with well defined emulsion droplet size. Example 8 was a thicker cream with smaller emulsion droplet size. Example 9 exhibited a gelling texture and strong film formation. Example 10 exhibited a bouncy gelling texture and enhanced film formation.

Emulsion Compositions: PPMA+APTES in Oil Phase and HA in Water Phase

Examples 11-13

| Phase | Chemical Name | Comparative Example 11 | Inventive Example 12 | Inventive Example 13 |
|---|---|---|---|---|
| A | Water | 50.00 | 50.00 | 50.00 |
| A | SODIUM HYALURONATE (HA) | 0.50 | 0.50 | 0.50 |
| B | Aminopropyl Triethoxysilane (APTES) | 0.00 | 0.25 | 0.50 |
| B | Isododecane | QS | QS | QS |
| B | Polyalkylene/Maleic Anhydride Copolymer* (PPMA) | 7.00 | 7.00 | 7.00 |

*PP207 is a linear polypropylene-ethylene-maleic anhydride copolymer wax commercially available from Clariant under the tradename LICOCARE PP207 LP 3349.

Procedure

For each composition, all ingredients in Phase A were added to a suitable size metal container. The contents were heated to 85 Celsius degrees or until all solids had melted.

All ingredients indicated in phase B were added to a suitable size side container B, and mixed until uniform. The contents were also heated to 85 Celsius degrees.

When both containers were at their proper temperatures, side container B was slowly added to main container A while mixing at high speed.

Contents were mixed at 80-85 Celsius degrees for 1 hour. Contents were cooled to 25 Celsius degree while mixing.

Comparative Example 11 showed clear separation once mixing was stopped. Inventive Example 12 formed a smooth cream that has good spreadability and film forming properties.

Inventive Example 13 formed a semi-solid gel that was bouncy and had very good film forming properties and water resistance.

Emulsion Compositions: PPMA+APTES in Oil Phase and APTES+HA in Water Phase

Examples 14-17

| Phase | Chemical Name | Inventive Example 14 | Inventive Example 15 | Inventive Example 16 | Inventive Example 17 |
|---|---|---|---|---|---|
| A | Water | 50.00 | 50.00 | 50.00 | 50.00 |
| A | SODIUM HYALURONATE (HA) | 0.50 | 0.50 | 0.50 | 0.50 |
| A | APTES | 0.05 | 0.13 | 0.38 | 0.75 |
| B | isododecane | QS | QS | QS | QS |
| B | Polyalkylene/Maleic Anhydride Copolymer* (PPMA) | 7.00 | 7.00 | 7.00 | 7.00 |
| B | APTES | 0.05 | 0.13 | 0.38 | 0.75 |

*PP207 is a linear polypropylene-ethylene-maleic anhydride copolymer wax commercially available from Clariant under the tradename LICOCARE PP207 LP 3349.

Procedure

For each composition, all ingredients in Phase A were added to a suitable size metal container. The contents were heated to 85 Celsius degrees or until all solids had melted.

All ingredients indicated in phase B were added to a suitable size side container B, and mixed until uniform. The contents were also heated to 85 Celsius degrees for 8 hrs.

When both containers were at their proper temperatures, side container B was slowly added to main container A while mixing at high speed.

Contents were mixed at 80-85 Celsius degrees for 1 hour.

Contents were cooled to 25 Celsius degree while mixing.

Inventive Example 14 was a light cream with well defined emulsion droplet size. Inventive Example 15 was a thicker cream with smaller emulsion droplet size. Inventive Example 16 exhibited a gelling texture and strong film formation. Inventive Example 17 exhibited a bouncy gelling texture and enhanced film formation.

What is claimed is:

1. A composition comprising water and a reaction product of at least one polar modified polymer and at least one alkoxysilane having at least one solubilizing functional group and at least one amino substituent,
   wherein the composition is in the form of an emulsion, and
   wherein the oil-soluble polar modified polymer comprises at least one C2-C4 monomer, is modified with at least one hydrophilic unit, and has a weight-average molecular weight of less than or equal to 25 000 g/mol and a melting point above 75° C.

2. The composition of claim 1, wherein the at least one polar modified polymer is a polypropylene and/or polyethylene-maleic anhydride modified wax.

3. The composition of claim 1, wherein the at least one alkoxysilane having at least one solubilizing functional group and at least one amino substituent is 3-aminopropyltriethoxysilane.

4. A composition comprising:
   (a) a reaction product of at least one polar modified polymer and at least one alkoxysilane having at least one solubilizing functional group and at least one amino substituent,
   wherein the oil-soluble polar modified polymer comprises at least one C2-C4 monomer, is modified with at least one hydrophilic unit, and has a weight-average molecular weight of less than or equal to 25 000 g/mol and a melting point above 75° C.; and
   (b) at least one oil carrier, wherein the at least one oil carrier is present in an amount of from about 1 to about 90% by weight, based on the total weight of the composition, and
   wherein the composition is anhydrous.

5. The composition of claim 4, wherein the at least one polar modified polymer is a polypropylene and/or polyethylene-maleic anhydride modified wax.

6. The composition of claim 4, wherein the at least one polar modified polymer is present in an amount of from about 1 to about 30% by weight, based on the total weight of the composition.

7. The composition of claim 4, wherein the at least one alkoxysilane having at least one solubilizing functional group and at least one amino substituent is 3-aminopropyltriethoxysilane.

8. The composition of claim 4, wherein the at least one alkoxysilane having at least one solubilizing functional group and at least one amino substituent is present in an amount of from about 0.01 to about 10% by weight, based on the total weight of the composition.

9. The composition of claim 4, wherein the at least one oil carrier is chosen from volatile oils and non-volatile oils.

10. The composition of claim 4, wherein the at least one oil carrier is present in an amount of from about 10% to about 85% by weight, based on the total weight of the composition.

11. The composition of claim 4, further comprising at least one colorant.

12. The composition of claim 4, further comprising hyaluronic acid.

13. The composition of claim 4, further comprising at least one surfactant.

14. The composition of claim 1, wherein the at least one polar modified polymer is present in an amount of from about 1 to about 30% by weight, based on the total weight of the composition.

15. The composition of claim 1, wherein the at least one alkoxysilane having at least one solubilizing functional group and at least one amino substituent is present in an amount of from about 0.01 to about 10% by weight, based on the total weight of the composition.

16. The composition of claim 1, wherein the composition further comprises at least one oil.

17. The composition of claim 1, wherein the at least one oil is present in an amount of from about 1 to about 90% by weight, based on the total weight of the composition.

18. The composition of claim 1, further comprising at least one colorant.

19. The composition of claim 1, further comprising hyaluronic acid.

20. The composition of claim 1, further comprising at least one surfactant.

* * * * *